United States Patent
Puglia et al.

(10) Patent No.: US 7,544,674 B2
(45) Date of Patent: Jun. 9, 2009

(54) TOPICAL SKIN CARE COMPOSITION

(75) Inventors: Nancy Puglia, Sanford, FL (US); Jerry Roth, Sanford, FL (US); Rosario Ramirez, Sanford, FL (US)

(73) Assignee: Galderma S.A., Cham (CH)

( * ) Notice: Subject to any disclaimer, the term of this patent is extended or adjusted under 35 U.S.C. 154(b) by 318 days.

(21) Appl. No.: 10/280,483

(22) Filed: Oct. 25, 2002

(65) Prior Publication Data

US 2004/0081668 A1    Apr. 29, 2004

(51) Int. Cl.
  A61K 31/58    (2006.01)
  A61K 31/075   (2006.01)
  A61K 31/05    (2006.01)

(52) U.S. Cl. .................. 514/172; 514/721; 514/731

(58) Field of Classification Search ........... 514/172, 514/731, 721
  See application file for complete search history.

(56) References Cited

U.S. PATENT DOCUMENTS

| | | | |
|---|---|---|---|
| 1,429,430 A | 10/1922 | Holmes et al. | |
| 2,164,723 A | 7/1939 | Schrauth et al. | |
| 3,226,295 A | 12/1965 | Goetz et al. | |
| 3,776,857 A | 12/1973 | Lindner | 252/308 |
| 3,856,934 A * | 12/1974 | Kligman | 424/62 |
| 3,906,108 A | 9/1975 | Felty | 424/318 |
| 3,966,924 A | 6/1976 | Fredriksson | |
| 4,146,499 A | 3/1979 | Rosano | 252/186 |
| 4,254,104 A | 3/1981 | Suzuki | 424/170 |
| 4,427,670 A | 1/1984 | Ofuchi et al. | 424/241 |
| 4,603,046 A * | 7/1986 | Georgalas et al. | 424/59 |
| 4,603,146 A * | 7/1986 | Kligman | 514/559 |
| 4,654,373 A | 3/1987 | Bertelli | |
| 4,737,360 A | 4/1988 | Allen et al. | |
| 4,857,321 A | 8/1989 | Thomas | |
| 4,992,478 A | 2/1991 | Geria | 514/782 |
| 5,145,604 A | 9/1992 | Neumiller | 252/312 |
| 5,514,698 A | 5/1996 | Ahmad et al. | 514/396 |
| 5,538,737 A | 7/1996 | Leonard et al. | 424/451 |
| 5,573,781 A | 11/1996 | Brown et al. | |
| 5,626,873 A | 5/1997 | Weiner et al. | |
| 5,645,854 A | 7/1997 | Masiz | |
| 5,651,991 A | 7/1997 | Sugiyama et al. | |
| 5,656,672 A | 8/1997 | Collin et al. | 514/725 |
| 5,660,837 A | 8/1997 | Lundquist | 424/400 |
| 5,744,148 A | 4/1998 | Habif et al. | 424/401 |
| 5,851,543 A | 12/1998 | Korb et al. | |
| 5,935,589 A | 8/1999 | Mulcherjee et al. | 424/401 |
| 5,951,993 A | 9/1999 | Scholz et al. | 424/405 |
| 5,962,512 A | 10/1999 | Goupil | |
| 5,976,555 A | 11/1999 | Liu et al. | 424/401 |
| 5,997,890 A | 12/1999 | Sine et al. | 424/401 |
| 6,001,377 A | 12/1999 | SaNogueira, Jr. et al. | 424/401 |
| 6,030,623 A | 2/2000 | Meade | |
| 6,080,393 A | 6/2000 | Liu et al. | 424/78.03 |
| 6,090,395 A | 7/2000 | Asmus et al. | 424/401 |
| 6,139,824 A | 10/2000 | Ribery et al. | 424/65 |
| 6,153,657 A | 11/2000 | Kisuno et al. | 516/925 |
| 6,174,533 B1 | 1/2001 | SaNogueira, Jr. et al. | 424/401 |
| 6,200,964 B1 * | 3/2001 | Singleton et al. | 514/159 |
| 6,267,985 B1 | 7/2001 | Chen et al. | |
| 6,365,656 B1 | 4/2002 | Green et al. | |
| 6,383,499 B1 | 5/2002 | Lipi | |
| 6,413,536 B1 | 7/2002 | Gibson | |
| 6,423,323 B2 | 7/2002 | Neubourg | |
| 2005/0101580 A1 | 5/2005 | Puglia et al. | |
| 2006/0099173 A1 | 5/2006 | Puglia et al. | |

FOREIGN PATENT DOCUMENTS

| | | |
|---|---|---|
| JP | 01-203036 A2 | 8/1989 |
| KR | 1999-0087346 | 12/1999 |
| KR | 2000-0073077 | 12/2000 |
| KR | 2001-0089781 | 10/2001 |
| WO | WO-03/055472 | 7/2003 |
| WO | WO-2004/021967 | 3/2004 |
| WO | WO 2004/037201 | 5/2004 |

OTHER PUBLICATIONS

FDA, Tri-Luma™ approval letter (Jan. 18, 2002).
Galderma Laboratories, Tri-Luma™ prescribing information (Jan. 2002).
PCT International Search Report dated Aug. 27, 2004.
Lack et al., New Eng J Med, 348(11):977-85 (2003).
Lever, B Med J, 313:299-300 (1996).
Taylor et al., J Allergy Clin Immunol, 68(5):372-75 (1981).
Gilbert, B., "TriLuma Combination Effective For PIH", Determatology Times, Sep. 1, 2005, pp. 1-2 (XP-002403792).
Cook-Bolden, F. et al., "The Use Of A Triple-Drug Combination Product and Procedures For The Treatment Of Hyperpigmentary Disorders", Cosmetic Dermatology, vol. 18, No. 8, pp. 589-594 (XP009066078).
Callender, V.D., "Acne In Ethnic Skin: Special Considerations For Therapy", Dermatologic Therapy, 2004 No. 2, vol. 17, pp. 184-195, Blackwell Publishing, Inc., US (XP-002383242).
Goodheart, H.P., "Hyperpigmentation Disorders", Women's Health In Primary Care, vol. 2, No. 12, Dec. 1999, pp. 923, 924, 929 (XP-002251799).
Momosawa, A. et al., "Combined Therapy Using Q-Switched Ruby Laser And Bleaching Treatment With Tretinoin And Hydroquinone For acquired Dermal Melanocytosis", Dermatologic Surgery, Oct. 1, 2003, vol. 29, No. 10, pp. 1001-1007; Blackwell Publishing, Inc., US (XP-002383243).

(Continued)

*Primary Examiner*—Sreeni Padmanabhan
*Assistant Examiner*—Renee Claytor
(74) *Attorney, Agent, or Firm*—Darby & Darby P.C.

(57) ABSTRACT

A cream base for the topical application of skin care therapeutics and a process for making the cream base. In one embodiment, the therapeutic is tretinoin, hydroquinone and fluocinolone acetonide for the treatment of hyperpigmented skin conditions, such as melasma.

21 Claims, No Drawings

OTHER PUBLICATIONS

Clark, J., "Cream Combo Called Melasma Drug Of Chorice", Dermatology Times, vol. 23 No. 5, May 1, 2002, pp. 1-2 (XP008062911).
Mosby, C.V., Journal Of The American Academy Of Dermatology, vol. 52, No. 3, Mar. 2005, p. 19.
Katsambas, A.D. et al., "Depigmenting and Bleaching Agents: coping With Hyperpigmentation", Clinics in Dermatology, vol. 19, 2001, pp. 483-488, Elsevier Science B.V.
Kang, S. et al., "Assessment Of Adapalene Gel For The Treatment Of Actinic Keratoses And Lentigines: A Randomized Trial", Journal Of The American Academy Of Dermatology, Jul. 2003, vol. 49, No. 1, pp. 83-90.
Milikan, L.E., "Adapalene: An Update On Newei Comparative Studies Between The Various Retinoids", International Journal of Dermatology, vol. 39, No. 10, 2000, pp. 784-788.
Gollnick, H. et al., "Topical Therapy In Acne", Journal Of European Academy Of Dermatology and Venereology, vol. 11, No. Supp. 1, Sep. 1998, pp. S08-S12, Elsevier Science B.V.
Torok, H.M., Hydroquinone 4%, Tretinoin 0.05%, Fluocinolone Acetonide 0.01%, Flucinolone Acetonide 0.01%: A Safe And Efficacious 12-Month Treatment For Melasma et al., Therapeutics For Clinician, vol. 75, No. 1, Jan. 2005, pp. 57-62.

* cited by examiner

TOPICAL SKIN CARE COMPOSITION

FIELD OF THE INVENTION

The invention relates generally to medicated skin treating compositions and more particularly to a cream containing a medicament for the treatment of a hyperpigmented skin condition.

BACKGROUND OF THE INVENTION

Melasma or chloasma is a common pigmentary condition that affects primarily women in their reproductive years. Dark, mottled (hyperpigmented) patches appear on the face and neck, especially on the cheeks and forehead. Melasma is usually triggered by hormonal activity that is the result of pregnancy or birth control pills. Thus, the condition is known as the "mask of pregnancy". The condition occurs when excess melanin is deposited in the cells of the epidermis and dermis. Melasma can persist for long periods of time and often recurs with subsequent pregnancies. The condition is less common among men, who account for about 10% of all cases.

Standard therapy involves depigmenting, or bleaching, the affected areas of the skin, the use of sunscreens, and avoidance of sunlight. Hydroquinone is the most popular topical depigmenting agent. Concentrations of 5%-10% hydroquinone are very effective, but can be irritating. The chemical stability of hydroquinone formulations is important because hydroquinone is easily oxidized and loses potency. The most commonly used agent usually involves a 16- to 20-week course of therapy, and some therapies can take longer. Tretinoin (Retin-A) is another widely used therapy for melasma.

Nevertheless, there remains a need in the art for a therapeutic approach that would contain several medicines for the treatment of melasma in a single composition. Moreover, it would be useful to have a therapeutic carrier, such as a cream, that would facilitate the penetration of the medicaments into the skin.

U.S. Pat. No. 5,538,737 discloses a method of making a water-in-oil emulsion containing a pharmaceutically acceptable salt of an $H_2$-antagonist. The steps include dissolving the pharmaceutically acceptable salt in an aqueous medium to form a water portion; combining the water portion with an oil portion, comprising an edible oil comprising an ester or mixed ester of glycerol and an emulsifying agent to form a water portion and oil portion matrix; then emulsifying the matrix to form the water-in-oil emulsion.

U.S. Pat. No. 5,656,672 discloses a process for preparing a water-in-oil emulsion with retinal as the active ingredient. The emulsion contains an oil phase including at least one organic solvent for retinal (such as aliphatic fatty alcohols) and optional lipophilic additives; an aqueous phase containing water and optional hydrophilic additives; and an agent for emulsifying the aqueous phase in the oil phase. The oil phase and the aqueous phase are independently prepared, and the aqueous phase is incorporated into the oil phase, with subsequent addition of a phase-containing retinol and its solvent.

U.S. Pat. No. 5,660,837 discloses a process for the preparation of a pharmaceutical formulation in the form of an oil-in-water emulsion. The steps of the process include of adding the emulsion-stabilizing surface active drug and an optimal conventional surfactant to a two-phase, oil-water system at room temperature; allowing the emulsion-stabilizing surface active drug to equilibrate at an interface; adding an agent giving isotonicity to the final formulation; and homogenizing by high pressure technique.

U.S. Pat. No. 5,976,555 discloses skin care compositions. An oil-in-water emulsion base contains retinoids; cetearyl alcohol and cetearyl glucoside or a mixture of a polyethylene glycol ethers of stearyl alcohol; cetyl alcohol, stearyl alcohol and mixtures thereof; a light, dry absorbable oil; and substantive, emollient oils or waxes.

U.S. Pat. No. 6,080,393 discloses a skin care composition comprising an oil-in-water emulsion with a therapeutically effective amount of a retinoid; wherein the oil phase comprising one or more oils, and an effective amount of at least one oil-soluble antioxidant; and wherein the composition comprises a corticosteroid.

Nevertheless, there remains a need in the art for a method of making a smoother cream base for the application of therapeutic agents for the treatment of melasma, which will facilitate the penetration of the medicaments into the skin.

SUMMARY OF THE INVENTION

The invention provides a cream base for the topical application of skin care therapeutics and a process for making the cream base. In one embodiment, the therapeutic is for the treatment of hyperpigmented skin conditions, such as melasma.

The process for making the cream base entails (a) mixing the hydrophilic compounds with water to form an aqueous phase; (b) mixing the hydrophobic compounds with methylglueth and glycerin to form a hydrophobic (non-aqueous or wax) phase; then (c) mixing the hydrophilic and hydrophobic phases to one another to form a biphasic mixture; and finally (d) adding the emulsifier to the biphasic mixture to form the emulsion. By mixing the emulsifier after the aqueous and non-aqueous phases have been mixed, the result is a smoother-textured cream that disappears upon application to skin, as compared to creams made by processes where the emulsifier was added to the aqueous or non-aqueous phases earlier in the process. Because the emulsifier is added as the final step, less wax is needed in making the cream, resulting in a "thinner" hydrophilic cream that disappears faster when applied to the skin, as compared to creams made by processes where the emulsifier was added to the aqueous or non-aqueous phases earlier in the process. Another advantage of the process of the invention is that by controlling the temperature at which the components, including hydroquinone, are added, the cream does not turn as brown, resulting in a more pleasing-colored product.

In one embodiment, the invention also provides a cream, which includes the inactive ingredients butylated hydroxytoluene, cetyl alcohol, citric acid, glycerin, glyceryl stearate, magnesium aluminum silicate, methyl gluceth-10, methylparaben, PEG-100 stearate, propylparaben, purified water, sodium metabisulfite, stearic acid, and stearyl alcohol. In particular embodiments, the cream is a carrier that contains as an active ingredient fluocinolone acetonide, hydroquinone, tretinoin and combinations thereof. For example, the cream can be Tri-Luma™ Cream, which is the first approved product to combine the standard depigmenting agent, hydroquinone, with tretinoin and a topical low-potency steroid that can be applied as a single preparation. The recommended course of therapy for Tri-Luma™ Cream is 8 weeks, and significant results have been seen after the first 4 weeks of treatment.

DETAILED DESCRIPTION OF THE INVENTION

In one embodiment of the invention, approximately 344.8 kg of water, 15.0 kg magnesium aluminum silicate, and 0.2 kg butylated hydroxytoluene are first combined and mixed at 75-80° C. to form the aqueous phase. The mixing can be by side scrape agitation at a fixed speed. The resulting aqueous phase is a suspension.

Second, approximately 20.0 kg of cetyl alcohol, 15.0 kg of stearic acid, 20.0 kg of stearyl alcohol, 25.0 kg of methyl gluceth-10, 0.9 kg of methylparaben, 0.1 kg of propylparaben, and 20.0 kg of glycerin are mixed together at medium speed at about 75-80° C. to form the non-aqueous phase. The mixing can be at medium speed in a Lightnin® mixer. The resulting non-aqueous phase is a suspension. The second step can be performed before, after or concurrently with the first step.

Then, the non-aqueous phase is added to the aqueous phase and the combined biphasic mixture is cooled to a temperature in the range of 68° C. to 72° C., or about 70° C., after which about 17.5 kg of Arlacel® 165, 0.25 kg tretinoin and 0.050 kg fluocinolone acetonide are added and stirred with cooling. When the mixture reaches 60° C., 0.25 kg citric acid is added with mixing and cooling. When the temperature reaches 55° C., 20.0 kg hydroquinone is added with mixing and cooling. When the temperature reaches about 50° C., the mixture is homogenized with a homogenizer, with continued cooling. When the mixture reaches 45° C., 1.0 kg of sodium metabisulfite is added with stirring and cooling. Typically, the sodium metabisulfite is added about 30 minutes after the addition of the hydroquinone. The mixing can be at fixed speed in a side scrape agitator. The resulting composition of matter is an emulsion, i.e., a cream.

The presence of sodium metabisulfite in the cream prevents the oxidation of hydroquinone. The addition of sodium metabisulfite as the cream is cooling advantageously results in a well-mixed composition of matter, with the sodium metabisulfite evenly mixed throughout the cream and preventing the oxidation of the hydroquinone throughout the cream. Another advantage of the process of the invention is that by controlling the temperature at which the components, including hydroquinone, are added, the cream does not turn as brown, resulting in a more pleasing-colored product.

We found that the addition of the emulsifier following the mixing of the non-aqueous and aqueous phases to be advantageous for the making of the pharmaceutical composition of the invention. When we attempted to make a cream product using a standard technique of adding the emulsifier to the non-aqueous phase and then mixing with the aqueous phase, we found that no emulsion formed. However, when we added the emulsifier to the mixture of the non-aqueous and aqueous phases with cooling, according to the method of the invention, we found that a useful emulsion did form. This emulsion formed even though the relative proportion of the non-aqueous and aqueous phases according to the successful method of the invention was the same as when an emulsion did not form using the standard technique of adding a non-aqueous phase containing an emulsifier to an aqueous phase.

The resulting TRI-LUMA™ Cream contains fluocinolone acetonide, hydroquinone and tretinoin in a hydrophilic cream base for topical application. Each gram of TRI-LUMA™ Cream contains as active ingredients, fluocinolone acetonide 0.01% (0.1 mg), hydroquinone 4% (40 mg), and tretinoin 0.05% (0.5 mg), and as inactive ingredients, butylated hydroxytoluene, cetyl alcohol, citric acid, glycerin, glyceryl stearate, magnesium aluminum silicate, methyl gluceth-10, methylparaben, PEG-100 stearate, propylparaben, purified water, sodium metabisulfite, stearic acid, and stearyl alcohol. See, TABLE 1.

TABLE 1

| Ingredient | 500 g Batch Quantity | 800 g Batch Quantity | Formula |
|---|---|---|---|
| magnesium aluminum silicate NF | 15 kg | 24 kg | 3.00% |
| butylated hydroxytoluene NF | 200 g | 320 g | 0.04% |
| cetyl alcohol NF | 20 kg | 32 kg | 4.00% |
| stearic acid NF | 15 kg | 24 kg | 3.00% |
| stearyl alcohol NF | 20 kg | 32 kg | 4.00% |
| methylparaben NF | 900 g | 1,440 g | 0.18% |
| propylparaben NF | 100 g | 160 g | 0.02% |
| Arlacel ® 165 [glycerol stearate and PEG-100 stearate glycerol monostearate] | 17.5 kg | 28 kg | 3.50% |
| methyl gluceth-10 | 25 kg | 40 kg | 5.00% |
| glycerin USP | 20 kg | 32 kg | 4.00% |
| tretinoin USP | 250 g | 400 g | 0.05% |
| fluocinolone acetonide USP | 50 g | 80 g | 0.01% |
| citric acid USP | 250 g | 400 g | 0.05% |
| hydroquinone USP | 20 kg | 32 kg | 4.00% |
| sodium metabisulfite NF | 1 kg | 1.6 kg | 0.20% |
| purified water USP | 344.8 kg | 551.6 kg | 68.95% |
| total | | | 100.00% |

Fluocinolone acetonide is a synthetic fluorinated corticosteroid for topical dermatological use and is classified therapeutically as an anti-inflammatory. It is a white crystalline powder that is odorless and stable in light. The chemical name for fluocinolone acetonide is (6,11,16)-6,9-difluoro-11,21-dihydroxy-16,17-[(1-methylethylidene)bis(oxy)]-pregna-1,-4-diene-3,20-dione. The molecular formula is $C_{24}H_{30}F_2O_6$ and molecular weight is 452.50.

Hydroquinone is classified therapeutically as a depigmenting agent. It is prepared from the reduction of p-benzoquinone with sodium bisulfite. It occurs as fine white needles that darken on exposure to air. The chemical name for hydroquinone is 1,4-benzenediol. The molecular formula is $C_6H_6O_2$ and molecular weight is 110.11.

Tretinoin is all-trans-retinoic acid formed from the oxidation of the aldehyde group of retinene to a carboxyl group. It is highly reactive to light and moisture. Tretinoin is classified therapeutically as a keratolytic. The chemical name for tretinoin is: (all-E)-3,7-dimethyl-9-(2,6,6-trimethyl-1-cyclohexen-1-yl)-2,4,6,8-nonatetraenoic acid. The molecular formula is $C_{20}H_{28}O_2$ and molecular weight is 300.44.

TRI-LUMA™ Cream is typically supplied in 30 g aluminum tubes, NDC 0299-5950-30, and is stored at controlled room temperature 68 to 77° F. (20-25° C.).

The details of one or more embodiments of the invention are set forth in the accompanying description above. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

The following EXAMPLES are presented to more fully illustrate the preferred embodiments of the invention. These EXAMPLES should in no way be construed as limiting the scope of the invention, as defined by the appended claims.

EXAMPLE I

Human Pharmacokinetics

Percutaneous absorption of unchanged tretinoin, hydroquinone and fluocinolone acetonide into the systemic circulation of two groups of healthy volunteers (Total n=59) was found to be minimal following 8 weeks of daily application of 1 g (Group I, n=45) or 6 g (Group II, n=14) of TRI-LUMA™ Cream.

For tretinoin quantifiable plasma concentrations were obtained in 57.78% (26 out of 45) of Group 1 and 57.14% (8 out of 14) of Group II subjects. The exposure to tretinoin as reflected by the $C_{max}$ values ranged from 2.01 to 5.34 ng/mL (Group I) and 2.0 to 4.99 ng/mL (Group II). Thus, daily application of TRI-LUMA™ Cream resulted in a minimal increase of normal endogenous levels of tretinoin. The circulating tretinoin levels represent only a portion of total tretinoin-associated retinoids, which would include metabolites of tretinoin and that sequestered into peripheral tissues.

For hydroquinone quantifiable plasma concentrations were obtained in 18% (8 out of 44) Group I subjects. The exposure to hydroquinone as reflected by the $C_{max}$ values ranged from 25.55 to 86.52 ng/mL. All Group II subjects (6 g dose) had undetectably low post-dose plasma concentrations.

For fluocinolone acetonide, Groups I and II subjects had undetectably low post-dose plasma concentrations.

The following tests may be helpful in evaluating patients: (a) ACTH or cosyntropin stimulation tests; (b) the A.M. plasma cortisol test; and (c) the urinary free cortisol test.

EXAMPLE II

Human Clinical Studies

Two efficacy and safety studies were conducted in 641 melasma patients between the ages of 21 to 75 years, having skin phototypes I-IV and moderate to severe melasma of the face. TRI-LUMA™ Cream was compared with three possible combinations of two of the three active ingredients [(1) hydroquinone 4% (HQ)+tretinoin 0.05% (RA); (2) fluocinolone acetonide 0.01% (FA)+tretinoin 0.05% (RA); (3) fluocinolone acetonide 0.01% (FA)+hydroquinone 4% (HQ)], contained in the same vehicle as TRI-LUMA™ Cream.

The patients were instructed to apply their study medication each night, after washing their face with a mild soapless cleanser, for 8 weeks. The patients were also instructed to apply a thin layer of study medication to the hyperpigmented lesion, making sure to cover the entire lesion including the outside borders extending to the normal pigmented skin. The patients were provided a mild moisturizer for use as needed and a sunscreen with SPF 30 for daily use. Moreover, the patients were instructed to avoid sunlight exposure to the face, wear protective clothing Protective clothing and avoidance of sunlight exposure to the face was recommended.

The patients were evaluated for melasma seventy at baseline and at weeks 1, 2, 4, and 8 of treatment. Primary efficacy was based on the proportion of patients who had an investigators' assessment of treatment success, defined as the clearing of melasma at the end of the eight-week treatment period. The majority of patients enrolled in the two studies were white (approximately 66%) and female (approximately 98%). TRI-LUMA™ Cream was demonstrated to be significantly more effective than any of the other combinations of the active ingredients.

Patients experienced improvement of their melasma with the use of TRI-LUMA™ Cream as early as 4 weeks. However, among 7 patients who had clearing at the end of 4 weeks of treatment with TRI-LUMA™ Cream, 4 of them did not maintain the remission after an additional 4 weeks of treatment.

After 8 weeks of treatment with the study drug, patients entered into an open-label extension period in which TRI-LUMA™ Cream was given on an as-needed basis for the treatment of melasma. In studies, after 8 weeks of treatment with TRI-LUMA™ Cream, most patients had at least some improvement. Some had their dark spots clear up completely (38% in one study and 13% in another). In most patients treated with TRI-LUMA™ Cream, their melasma came back after treatment. The remission periods appeared to shorten between progressive courses of treatment. Additionally, few patients maintained complete clearing of melasma (approximately 1 to 2%).

TABLE 2

Investigators' Assessment of Treatment Success*
At the End of 8 Weeks of Treatment

|  |  | TRI-LUMA ™ Cream | HQ + RA | FA + RA | FA + HQ |
|---|---|---|---|---|---|
| Study No. 1 | Number of Patients | 85 | 83 | 85 | 85 |
|  | Number of Successes | 32 | 12 | 0 | 3 |
|  | Proportion of Successes | 38% | 15% | 0% | 4% |
|  | P-value |  | <0.001 | <0.001 | <0.001 |
| Study No. 2 | Number of Patients | 76 | 75 | 76 | 78 |
|  | Number of Successes | 10 | 3 | 3 | 1 |
|  | Proportion of Successes | 13% | 4% | 4% | 1% |
|  | P-value[#] |  | 0.045 | 0.042 | 0.005 |

*Treatment success was defined as melasma severity score of zero (melasma lesions cleared of hyperpigmentation).
[#]P-value is from Cochran-Mantel-Haenszel chi-square statistics controlling for pooled investigator and comparing TRI-LUMA ™ Cream to the other treatment groups.

Based on melasma severity at the beginning of the trial, 161 patients were assessed for improvement at day 56 of treatment. 61% (99 patients) experienced symptom improvement from "moderate" to "mild" or "cleared", and 68% (25) showed improvement from "severe" to "mild" or "cleared" over the 8-week treatment period as shown in TABLE 3.

TABLE 3

Investigators' Assessment of Change in Melasma Severity from Baseline to Day 56 of Treatment (combined results from studies 1 and 2)

| | Baseline | | Number (%) of Patients at Day 56[a] | | | | |
|---|---|---|---|---|---|---|---|
| | Severity Rating | N | Cleared[b] N (%) | Mild[b] N (%) | Moderate[b] N (%) | Severe[b] N (%) | Missing[b] N (%) |
| Tri-Luma ™ Cream | Moderate | 124 | 36 (29) | 63 (51) | 18 (16) | 0 (0) | 7 (6%) |
| | Severe | 37 | 6 (16) | 19 (51) | 9 (24) | 2 (5) | 1 (3%) |

N = 161
[a]Assessment based on patients with severity scores at day 56. Percentages are based on the total number in the treatment group population.
[b]Does not include patients who cleared before day 56 or were missing from the day 56 assessment. Assessment scale: Cleared (melasma lesions approximately equivalent to surrounding normal skin or with minimal residual hyperpigmentation); Mild (slightly darker than the surrounding normal skin); Moderate (moderately darker than the surrounding normal skin); Severe (markedly darker than the surrounding normal skin).

EXAMPLE III

Averse Reactions in Humans

In a patch test study to determine sensitization potential in 221 healthy volunteers, three volunteers developed sensitivity reactions to TRI-LUMA Cream or its components.

In the controlled clinical trials, adverse events were monitored in the 161 patients who used TRI-LUMA™ Cream once daily during an 8-week treatment period. There were 102 (63%) patients who experienced at least one treatment-related adverse event during these studies. The most frequently reported events were erythema, desquamation, burning, dryness, and pruritus at the site of application. The majority of these events were mild to moderate in severity. Adverse events reported by at least 1% of patients and judged by the investigators to be reasonably related to treatment with TRI-LUMA™ Cream from the controlled clinical studies are summarized (in decreasing order of frequency) as follows:

TABLE 4

Incidence and Frequency of Treatment-Related Adverse Events with TRI-LUMA ™ Cream In At Least 1% or More of Patients (N = 161)

| Adverse Event | Number | (%) of Patients |
|---|---|---|
| Erythema | 66 | (41%) |
| Desquamation | 61 | (38%) |
| Burning | 29 | (18%) |
| Dryness | 23 | (14%) |
| Pruritus | 18 | (11%) |
| Acne | 8 | (5%) |
| Paresthesia | 5 | (3%) |
| Telangiectasia | 5 | (3%) |
| Hyperesthesia | 3 | (2%) |
| Pigmentary changes | 3 | (2%) |
| Irritation | 3 | (2%) |
| Papules | 2 | (1%) |
| Acne-like rash | 1 | (1%) |
| Rosacea | 1 | (1%) |
| Dry mouth | 1 | (1%) |
| Rash | 1 | (1%) |
| Vesicles | 1 | (1%) |

In an open-label long-term safety study, patients who have had cumulative treatment of melasma with TRI-LUMA™ Cream for 6 months showed a similar pattern of adverse events as in the 8-week studies. The following local adverse reactions have been reported infrequently with topical corticosteroids. They may occur more frequently with the use of occlusive dressings, especially with higher potency corticosteroids. These reactions are listed in an approximate decreasing order of occurrence: burning, itching, irritation, dryness, folliculitis, acneiform eruptions, hypopigmentation, perioral dermatitis, allergic contact dermatitis, secondary infection, skin atrophy, striae, and miliaria.

The foregoing description has been presented only for the purposes of illustration and is not intended to limit the invention to the precise form disclosed, but by the claims appended hereto.

What is claimed is:

1. A method of making a topical medicated composition comprising water, hydrophilic compounds and hydrophobic compounds, and active ingredients consisting of fluocinolone acetonide, hydroquinone and tretinoin, the method comprising:
    (a) mixing water and at least one hydrophilic compound to form an aqueous composition;
    (b) mixing at least two hydrophobic compounds to form a non-aqueous composition;
    (c) mixing the aqueous composition and the non-aqueous composition to form a mixture, said steps (a) through (c) being conducted in the absence of an emulsifier;
    (d) mixing the fluocinolone acetonide and the tretinoin into the mixture of step (c);
    (e) adding at least one emulsifier after step (c) into the mixture of step (c), or during step (d); and thereafter
    (f) homogenizing the mixture;
    wherein the hydroquinone is added in step (d) after adding the at least one emulsifier.

2. The method of claim 1, wherein said aqueous composition comprises, magnesium aluminum silicate and butylated hydroxytoluene.

3. The method of claim 1, wherein said non-aqueous composition comprises at least two hydrophobic compounds selected from the group consisting of cetyl alcohol, stearic acid, stearyl alcohol, methyl gluceth, methylparaben, propylparaben and glycerin.

4. The method of claim 3, wherein said non-aqueous composition comprises cetyl alcohol, stearic acid, stearyl alcohol, methyl gluceth, methylparaben, propylparaben and glycerin.

5. The method of claim 1, wherein said at least one emulsifier is glyceryl stearate, polyethylene glycol (PEG) stearate or a combination thereof.

6. The method of claim 5, wherein said at least one emulsifier is a combination of glyceryl stearate and polyethylene glycol stearate.

7. The method of claim 1, further comprising adding sodium metabisulfite to said mixture of step (e) after adding said at least one emulsifier.

8. The method of claim 1, wherein said water and said at least one hydrophilic compound are mixed at an elevated temperature.

9. The method of claim 8, wherein said elevated temperature is from about 75° C. to about 80° C.

10. The method of claim 1, wherein said at least two hydrophobic compounds are mixed at an elevated temperature.

11. The method of claim 10, wherein said elevated temperature is from about 75° C. to about 80° C.

12. The method of claim 1, wherein said water and said at least one hydrophilic compound are mixed at a temperature of from about 75° C. to about 80° C., and said at least two hydrophobic compounds are mixed at a temperature of from about 75° C. to about 80° C.

13. The method of claim 12, wherein said mixture of step (c) is cooled before adding said fluocinolone acetonide and said tretinoin in step (d).

14. The method of claim 13, wherein said cooled temperature is from about 68° C. to about 72° C.

15. The method of claim 12, wherein said mixture of step (d) is cooled while the at least one emulsifier is mixed into the mixture of step (d).

16. The method of claim 12, wherein the hydroquinone is added in step (d) after the mixture of tretinoin and fluocinolone acetonide is cooled.

17. The method of claim 16, wherein said mixture is cooled to about 55° C. before adding said hydroquinone.

18. The method of claim 12, wherein said homogenizing step (f) occurs at a temperature of about 50° C.

19. The method of claim 18, wherein sodium metabisulfite is added to the homogenized mixture after the hydroquinone is added and after the homogenized mixture is cooled to about 45° C.

20. A method of making a topical medicated composition comprising water, hydrophilic compounds and hydrophobic compounds, and active ingredients consisting of fluocinolone acetonide, hydroquinone and tretinoin, the method comprising:
  (a) mixing water and at least one hydrophilic compound to form an aqueous composition comprising magnesium aluminum silicate and butylated hydroxytoluene;
  (b) mixing at least two hydrophobic compounds to form a non-aqueous composition, wherein the hydrophobic compounds are selected from the group consisting of cetyl alcohol, stearic acid, stearyl alcohol, methyl gluceth, methylparaben, propylparaben, and glycerin;
  (c) mixing the aqueous composition and the non-aqueous composition to form a mixture, said steps (a) through (c) being conducted in the absence of an emulsifier;
  (d) mixing the fluocinolone acetonide and the tretinoin into the mixture of step (c);
  (e) adding at least one emulsifier after step (c) into the mixture of step (c), or during step (d); and thereafter
  (f) homogenizing the mixture;
wherein the hydroquinone is added in step (d) after adding the at least one emulsifier.

21. The method of claim 20, wherein at least one emulsifier is glyceryl stearate, polyethylene glycol (PEG) stearate or a combination thereof.

* * * * *